(12) United States Patent
Al Marzouqi et al.

(10) Patent No.: US 9,957,026 B2
(45) Date of Patent: May 1, 2018

(54) DEVICE FOR PROVIDING BUOYANCY

(71) Applicant: United Arab Emirates University, Al Ain (AE)

(72) Inventors: Ali Al Marzouqi, Al Ain (AE); Mahmoud Al Ahmad, Al Ain (AE); Shamsa Aldhaheri, Al Ain (AE); Ghubaisha Slayem Al Ameri, Al Ain (AE); Maryam Abdullah Al Jabri, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days. days.

(21) Appl. No.: 15/122,008

(22) PCT Filed: Sep. 16, 2014

(86) PCT No.: PCT/IB2014/064559
§ 371 (c)(1),
(2) Date: Aug. 26, 2016

(87) PCT Pub. No.: WO2016/042358
PCT Pub. Date: Mar. 24, 2016

(65) Prior Publication Data
US 2017/0190399 A1    Jul. 6, 2017

(51) Int. Cl.
*B63C 9/08*    (2006.01)
*B63C 9/18*    (2006.01)
(Continued)

(52) U.S. Cl.
CPC .............. *B63C 9/18* (2013.01); *A61B 5/145* (2013.01); *A61B 5/14542* (2013.01);
(Continued)

(58) Field of Classification Search
CPC ................................. B63C 9/18; A61B 5/145
See application file for complete search history.

(56) References Cited

U.S. PATENT DOCUMENTS 5,370,147 A * 12/1994 Brusse ...................... F16K 7/10
137/15.11
2009/0280705 A1    11/2009 Puls et al.
2010/0167608 A1    7/2010 Daye et al.

FOREIGN PATENT DOCUMENTS

WO    1997/047519 A1    12/1997
WO    2013/164864 A1    11/2013

OTHER PUBLICATIONS

International Search Report, International Patent Application No. PCT/IB2014/064559, dated Jan. 12, 2015, 4 pages.
(Continued)

*Primary Examiner* — Stephen P Avila
(74) *Attorney, Agent, or Firm* — Fitch, Even, Tabin & Flannery LLP

(57) ABSTRACT

A device for providing buoyancy comprising; —a bladder capable of being inflated; —a vessel containing fluid for inflating the bladder; and —one or more valves for controlling the passage of fluid between the bladder and the vessel; wherein one or more of the valves are capable of being opened to permit the passage of fluid from the vessel to the bladder in response to at least one of exposure of the device to a pre-determined pressure level and detection of blood oxygen concentration below a pre-determine threshold in an individual using the device.

18 Claims, 3 Drawing Sheets

(51) Int. Cl.
*A61B 5/145* (2006.01)
*A61B 5/00* (2006.01)
*A61B 5/0205* (2006.01)
*A61B 5/08* (2006.01)
*A61B 5/1455* (2006.01)

(52) U.S. Cl.
CPC .......... *A61B 5/0205* (2013.01); *A61B 5/0816* (2013.01); *A61B 5/14551* (2013.01); *A61B 5/7203* (2013.01)

(56) References Cited

OTHER PUBLICATIONS

Written Opinion of the International Searching Authority, International Patent Application No. PCT/IB2014/064559, dated Jan. 12, 2015, 6 pages.

* cited by examiner

DEVICE FOR PROVIDING BUOYANCY

BACKGROUND OF THE PRESENT INVENTION

Technical Field

This invention relates to a device for providing buoyancy.

Description of the Related Art

A number of devices have been proposed to provide buoyancy for the purpose of preventing the individual wearing the device from drowning. These personal flotation devices come in various forms and include life jackets, life vests, buoyancy aids and flotation suits. Some of these personal flotation devices have a foam core which provides the buoyancy whereas for others buoyancy is provided by air chambers contained within the device. For some of the devices containing air chambers these are inflated prior to the user coming into contact with water whereas others inflate only when the device is exposed to water.

SUMMARY OF THE PRESENT INVENTION

This invention provides a device for providing buoyancy comprising; a bladder capable of being inflated, a vessel containing fluid for inflating the bladder and one or more valves for controlling the passage of fluid between the bladder and the vessel; wherein the one or more valves are capable of being opened to permit the passage of fluid from the vessel to the bladder in response to at least one of exposure of the device to a pre-determined pressure level and detection of a blood oxygen concentration below a pre-determined threshold in an individual using the device.

In an embodiment of the invention, the device further comprises an actuator capable of being activated to open a valve upon being exposed to a pre-determined pressure level.

In a further embodiment of the invention, the device further comprises an oxymeter capable of causing a valve to open upon detecting blood oxygen concentration below a pre-determined threshold in the blood of the individual.

In a further embodiment of this invention, at least one of the actuator is adjustable to alter the pressure level at which activation occurs and the oxymeter is adjustable to alter the pre-determined oxygen concentration at which it causes a valve to open.

In a further embodiment of the invention, the actuator comprises a resilient member capable of being compressed by pressure thereby activating the actuator.

In a further embodiment of the invention, the actuator comprises a plug magnetically attracted to the interior surface of a conduit or to a component positioned within the conduit and wherein the plug is capable of being dislodged by pressure thereby activating the actuator.

In a further embodiment of the invention, the thickness of the plug is capable of being selected to determine the pressure required to dislodge the plug.

In a further embodiment of the invention, the weight of the plug is capable of being selected to determine the pressure required to dislodge the plug.

In a further embodiment of the invention, the magnetic field strength between the plug and the conduit or between the plug and the component positioned within the conduit is capable of being selected to determine the pressure required to dislodge the plug.

In a further embodiment of the invention, the bladder is in the form of a jacket for wearing by an individual.

In a further embodiment of the invention, the vessel contains compressed fluid capable of being released into the bladder as a gas.

In a further embodiment of the invention, one or more of the valves are capable of being opened by exposure to liquid released by at least one of activation of the actuator and detection of blood oxygen concentration below the pre-determined threshold by the oxymeter.

This invention further provides a method for providing buoyancy comprising; providing a bladder for inflating, providing a vessel containing fluid for inflating the bladder and controlling the passage of fluid between the bladder and the vessel with one or more valves; further comprising opening one or more of the valves to permit the passage of fluid from the vessel to the bladder in response to at least one of exposing the device to a pre-determined pressure level and detecting a blood oxygen concentration below a pre-determined threshold in an individual using the device.

In a further embodiment of the invention, the method further comprises providing an actuator capable of being activated to open a valve upon being exposed to a pre-determined pressure level.

In a further embodiments of the invention, the method further comprises providing an oxymeter capable of causing a valve to open upon detecting blood oxygen concentration below a pre-determined a pre-determined threshold in the blood of the individual.

In a further embodiment of the invention, the method further comprises adjusting at least one of the actuator to alter the pressure level at which activation occurs and the oxymeter to alter the pre-determined oxygen concentration at which it causes a valve to open.

In a further embodiment of the invention, the method further comprises providing an actuator comprising a resilient member capable of being compressed by pressure for activating the actuator.

In a further embodiment of the invention, the method further comprises providing an actuator comprising a plug which is magnetically attracted to the interior surface of a conduit or to a component positioned within the conduit and wherein the plug is capable of being dislodged by pressure for activating the actuator.

In a further embodiment of the invention, the method further comprises selecting the thickness of the plug to determine the pressure required to dislodge the plug.

In a further embodiment of the invention, the method further comprises selecting the weight of the plug to determine the pressure required to dislodge the plug.

In a further embodiment of the invention, the method further comprises selecting the magnetic field strength between the plug and the conduit or between the plug and the component positioned within the conduit to determine the pressure required to dislodge the plug.

In a further embodiment of the invention, the method further comprises providing a bladder formed as a jacket for wearing by an individual.

In a further embodiment of the invention, the method further comprises containing compressed fluid in the vessel for releasing into the bladder as a gas.

In a further embodiment of the invention, the method further comprises providing one or more valves which are capable of being opened by exposure to liquid released by at least one of activation of the actuator and detection of blood oxygen concentration below the pre-determined threshold by the oxymeter.

BRIEF DESCRIPTION OF THE DRAWINGS

The invention will now be described by way of example with reference to the accompanying drawings, in which.

DETAILED DESCRIPTION OF THE PRESENT INVENTION

Figure 1:
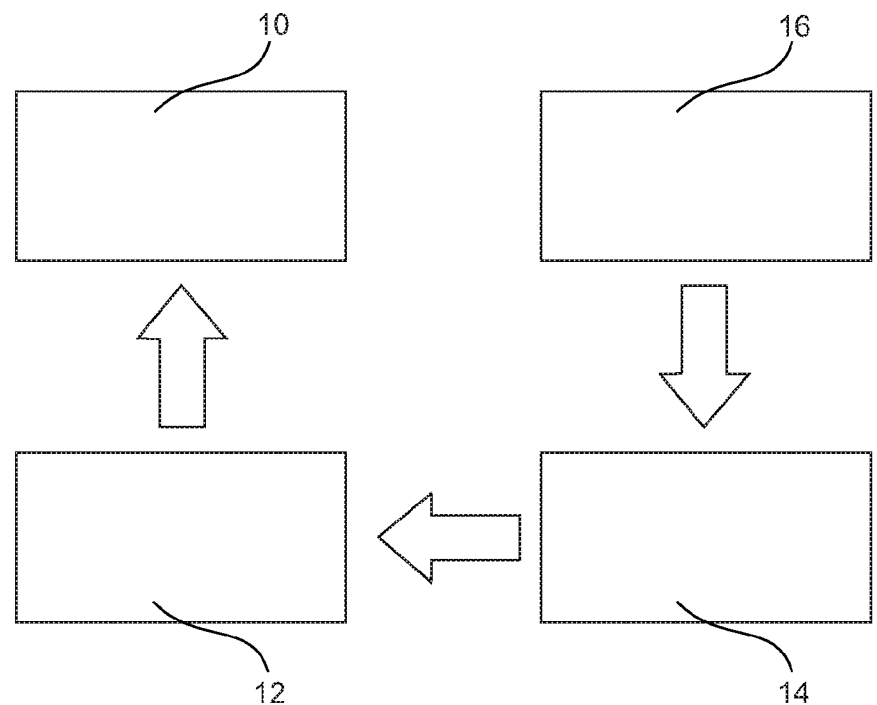
FIG. 1 shows a schematic view of the invention.

FIG. 1 shows a schematic view of the invention. This invention provides a device for providing buoyancy comprising a bladder (10) which is capable of being inflated, a vessel (12) containing fluid for inflating the bladder, one or more valves (14) for controlling the passage of fluid between the bladder and the vessel, and means (16) for opening one or more of the valves. Each valve is capable of being opened to permit the passage of fluid from the vessel to the bladder in response to at least one of exposure of the device to a pre-determined pressure level and detection of a blood oxygen concentration below a pre-determined threshold in an individual using the device.

This invention further provides, a system for providing buoyancy comprising the device and an attachment for securing the device to an individual. The device is therefore capable of being worn by an individual and is for providing buoyancy in the event that the individual becomes submerged in water or any other liquid. When the individual wearing the device is exposed to a pre-determined pressure level and/or a blood oxygen concentration below a pre-determined threshold is detected in the blood of an individual wearing the device one or more of the valves open. The opening of one or more of the valves in turn causes the vessel to release fluid into the bladder which inflates thereby providing buoyancy to the individual wearing the device.

The bladder can be of any form that is capable of being inflated with gas and which is impermeable so that the gas cannot escape once the bladder has been inflated. The bladder may be any shape or form that would be suitable for providing buoyancy of the individual wearing the device when they are in water. Preferably the bladder will contain multiple chambers to provide for redundancy in the event that one of the other chambers becomes damaged and thus will not inflate.

Preferably the attachment means for attaching the device to an individual will be the bladder itself and will be in a form that is capable of being worn by the individual. Should the individual fall into water and the bladder inflates it is preferable that the bladder is placed in a position relative to the individual's body so that the individual's head remains above water. Ideally the bladder will be attached in close proximity to the individual's upper body. In an embodiment of the invention the bladder is in the form of a jacket for wearing by an individual around their torso. The jacket may be any shape or size that is capable of being worn by an individual and could be T-shirt shaped or alternatively it could be in the form of a vest or sleeveless top. In an alternative embodiment of the invention the bladder is formed as a belt or ring for wearing around the torso of an individual.

The bladder should be formed of a material that is sufficiently light to provide buoyancy of an individual wearing the device when the bladder is inflated. Ideally the bladder should be made from a flexible material so that it is capable of existing in a compact form when the bladder is not inflated. Preferably the bladder will be made from a flexible polymer material, for example nylon. The bladder may also have a protective outer coating to prevent the bladder from being punctured or otherwise damaged, the outer coating may be formed of vinyl for example.

The vessel for containing the fluid for inflating the bladder can be any form of container or canister which is capable of holding fluid. Preferably the vessel contains compressed fluid which is capable of being released into the bladder as a gas by decompression of the fluid. Compressed fluid is preferable as less space is required to contain the fluid in the vessel and thus it is possible to have a smaller and lighter vessel. An example of a suitable fluid is carbon dioxide as it can be easily compressed when contained within the vessel and is capable of being released as a gas upon decompression.

The vessel should be formed of a material that is sufficiently strong to withstand high pressures. In the event that an individual wearing the device is submerged in water, the vessel needs to be strong enough to withstand exposure to the pressure levels found at some depth below the surface of the water. In the embodiment of the invention where the vessel contains compressed gas, the vessel also needs to be sufficiently strong to withstand the pressure of holding the compressed gas in question. The vessel should be large enough to contain sufficient fluid to be able to fully inflate the bladder upon activation.

Each valve is for controlling the passage of fluid between the vessel and the bladder. In the open position a valve permits the passage of fluid between the bladder and the vessel whereas in the closed position the passage of fluid is prevented. Each valve is capable of being opened in response to at least one of exposure of the device to a pre-determined pressure level and detection of a blood oxygen concentration below a pre-determined threshold in an individual using the device.

In an embodiment of the invention one or more of the valves is a pneumatic valve. In a further embodiment of the invention one or more of the valves are capable of being opened by exposure to liquid. In one example of this embodiment, the valve provided is in the form of polymer which is capable of being dissolved upon exposure to liquid which exposes an aperture previously covered by the polymer. A compressed spring is then able to extend out through the aperture and this in turn pushes the release mechanism on the vessel which expels gas causing the bladder to inflate.

Figure 2:
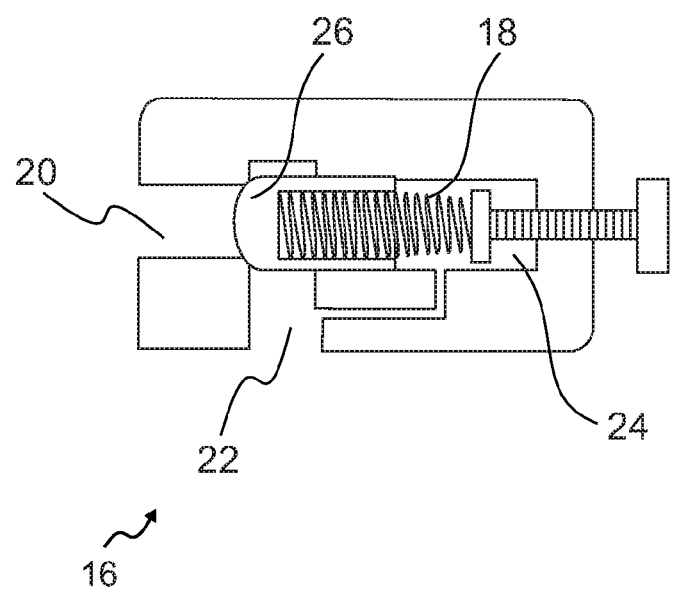
FIG. 2 shows an embodiment of the invention where the actuator comprises a resilient member in the form of a spring.

In an embodiment of the invention, the means (16) are embodied in an actuator, as shown in FIG. 2. The actuator is capable of being activated to open a valve upon being exposed to a pre-determined pressure level. The actuator and the valve which it activates may be separate components, alternatively they may be formed as a single integrated component. The actuator provides one mechanism for opening a valve to permit the passage of fluid from the vessel to the bladder. The actuator is capable of being adjusted to activate at a fixed level of pressure. When the actuator is exposed to this pressure level it will open a valve causing the bladder to inflate, irrespective of whether the person wearing the device is drowning or not. In an embodiment of the invention the actuator is adjustable to alter the pressure level at which activation occurs. For example the actuator can be configured to be activated at 1.1 bars of pressure, this corresponds to being approximately 1 meter underwater.

In one embodiment of the invention the actuator comprises a resilient member (18) capable of being compressed by pressure which causes the actuator to become activated. The resilient member may be a spring, memory shape material or any other material or mechanism capable of being compressed by pressure and further capable of returning to its original form when not being compressed.

FIG. 2 shows an embodiment of the invention where the actuator comprises a resilient member in the form of a spring. The actuator further comprises a fluid inlet (20) and a fluid outlet (22). The spring extends throughout a shaft (24) formed within the body of the actuator abutting against the end of the shaft at one end and having a cap (26) on the other end. The resilience of the spring is selected so that it will only compress to a threshold level when subjected to pressure at the inlet at the predetermined level. For example where the spring is adjusted to compress at 1.1 bars of pressure, the spring will compress to the threshold level once the device is placed 1 meter or more underwater. In this embodiment of the invention the actuator becomes activated when the spring is sufficiently far compressed within the shaft to the threshold level such that a flow path opens up between the inlet and the outlet. Water is then able to flow through the actuator and out of the outlet to a valve which opens when it is exposed to the water.

Figure 3:
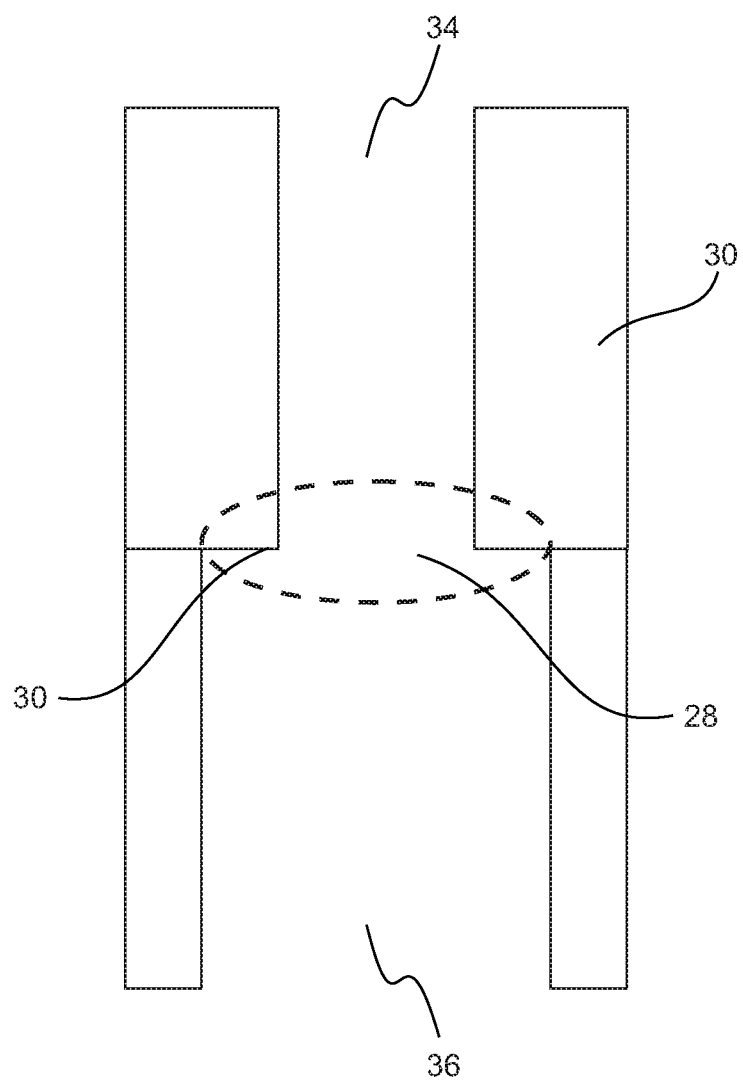
FIG. 3 shows an embodiment of the invention where the actuator comprises a plug magnetically attracted to the interior surface of the conduit.

In another embodiment of the invention the actuator comprises a plug (28) magnetically attracted to the interior surface of a conduit (30) or to a component (32) positioned within the conduit and wherein the plug is capable of being dislodged by pressure thereby activating the actuator. An example of this embodiment is shown in FIG. 3 where the conduit has an inlet (34) and an outlet (36). In this example, the inner surface of the conduit is staggered and the plug is magnetically attracted to the inner surface of the conduit, in this instance it is magnetically attracted to the protruding section.

The plug is capable of being dislodged from being in contact with the inner surface of the conduit or from being in contact with a component positioned within the conduit. This is achieved when the pressure pushing against the plug at the inlet of the actuator is of a greater force than the magnetic attraction between the plug and the inner surface of the conduit or component placed within. The pressure level at which the force becomes stronger than the magnetic attraction, and hence the point at which the plug dislodges, is capable of being adjusted. In one embodiment of the invention, the thickness of the plug is selected to determine the pressure required to dislodge the plug. In another embodiment of the invention, the weight of the plug is selected to determine the pressure required to dislodge the plug. In yet another embodiment of the invention, the magnetic field strength between the plug and the conduit or the component positioned within the conduit is selected to determine the pressure required to dislodge the plug.

Figure 4A:
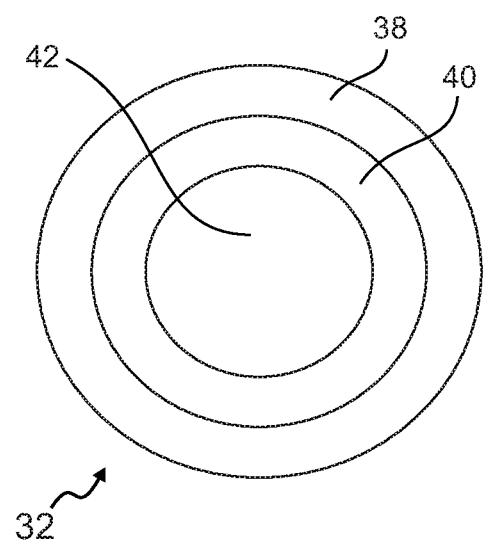
FIG. 4A shows a component capable of being positioned within the conduit.
Figure 4B:
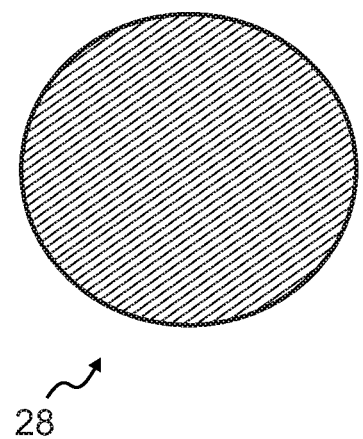
FIG. 4B shows a magnetic disk in an embodiment of the invention where the actuator comprises a plug magnetically attracted to a component positioned within the conduit.

FIG. 4A shows a component capable of being positioned within the conduit and FIG. 4B shows a plug in the form of a magnetic disk. The component is capable of being positioned within the conduit and should be fixed in place so that it cannot be dislodged by pressure.

The example of a component for positioning in the conduit shown in FIG. 4A comprises an outer ring (38), formed from a material that is capable of being fixed to the interior of the conduit, and an inner ring (40) formed from a metal. The component also has an opening (42) through which fluid is able to pass. FIG. 4B shows an example of a plug which is compatible with the component shown in FIG. 4A. The example of the plug shown in FIG. 4B is a disk having a metallic field, the metallic inner ring of the component is magnetically attracted to the disk. In an alternative embodiment the inner ring of the component possesses a magnetic field, the plug is formed from metal and is magnetically attracted to the inner ring. In yet a further embodiment both the component and the plug possess magnetic fields and are magnetically attracted to each other. In use the plug is magnetically attracted to the inner ring of the component thereby preventing the passage of fluid. Once pressure of a pre-determined level pushes onto the plug such that the force is greater than the magnetic attraction, the plug becomes dislodged and the passage of fluid along the conduit is permitted and this in turn opens a valve.

In an embodiment of the invention, the means (16) are embodied in an oxymeter capable of causing a valve to open upon detecting blood oxygen concentration below a pre-determined threshold in the blood of the individual. The oxymeter and the valve upon which it acts may be separate components. Alternatively, they may be formed as a single integrated component. This invention also provides a mechanism where the measurement of a low blood oxygen concentration by the oxymeter causes a valve to open. The oxymeter is capable of measuring oxygen concentration in the blood of an individual and is capable of causing a valve to open upon detecting that the measured oxygen concentration has dropped below a pre-determined concentration threshold. Whenever a valve is opened by this mechanism, this enables the passage of fluid from the vessel to the bladder causing the bladder to inflate.

In one embodiment of the invention the means will incorporate an actuator only and not an oxymeter. In another embodiment of the invention the means will incorporate an oxymeter only and not an actuator. In yet a further embodiment of the invention the means will incorporate both an actuator and an oxymeter; in this embodiment one or more of the valves are capable of being opened by the two different mechanisms.

The oxymeter may be any device capable of monitoring blood oxygen concentration in blood flowing from the lungs to the bodily tissues (i.e. blood that is oxygenated in a healthy individual). Preferably the blood oxygen concentration measurement taken will be a measurement of the percentage of haemoglobin binding sites occupied by oxygen molecules. Preferably the oxymeter is a pulse oxymeter; this is a non-invasive method of measuring blood oxygen concentration which allows for real time monitoring.

In one embodiment of the invention, the pre-determined blood oxygen concentration will be a percentage concentration. The pre-determined blood oxygen concentration is capable of being selected and preferably the concentration range of a healthy individual is taken into consideration. Ideally the pre-determined concentration should be set at a level which is less than the normal range because at this point there is a strong possibility that the individual in question is experiencing respiratory problems. The pre-determined blood oxygen concentration could be set at a higher percentage (i.e. at a concentration close to the normal range) where a more responsive inflation mechanism is required or it could be set at a lower percentage if it is important that the bladder does not inadvertently inflate in a non-emergency situation.

In a further embodiment of the invention, the oxymeter can be configured to monitor the blood oxygen concentration of the individual wearing the device when the individual is not experiencing respiratory difficulties to determine the base line level for that individual. The pre-determined concentration can then be chosen based upon this measurement, i.e. by selecting a concentration below the individual's normal range.

In the embodiment of the invention where the device incorporates an oxymeter, the oxymeter is capable of detecting where the blood oxygen concentration in the blood of an individual has dropped below the pre-determined threshold. The oxymeter detection mechanism may, for example, involve determining the presence or absence of such an event through a detection sequence. In the first step of such a detection sequence, a signal is output from the oxymeter and is sent to a signal conditioning unit. Ideally the signal is an electric signal. The signal conditioning unit is capable of amplifying input signal to increase the signal to noise ratio and is also capable of increasing the amplitude of the signal for processing. The signal conditioning unit is also capable of filtering the signal to attenuate background noise. In the next step in the sequence, the signal is fed through an analogue to digital converter for converting the signal into digital signal. In the final step of the sequence the signal is fed through a signal processing unit which is capable of analysing the signal to determine certain parameters based on the measured signal. Ideally the signal will have been amplified by the signal conditioning unit such that the parameters in the signal are accentuated and hence easier to detect by the signal processing unit. In this embodiment of the invention, the parameters are indicative of the blood oxygen concentration in the blood of an individual.

In the embodiment of the invention where the device incorporates an oxymeter and a blood oxygen concentration below the pre-determined threshold is detected in the blood of an individual, this initiates an activation mechanism for opening the valve. The activation mechanism may, for example, be an activation sequence. In the first step of such a sequence a signal is output from the signal processing unit in the event that a blood oxygen concentration below the pre-determined threshold has been detected by the oxymeter. Ideally the signal is an electric signal. The output signal is sent to a digital to analogue converter for converting the signal into analogue signal. In the next step the signal is fed through a signal conditioning unit which is capable of amplifying the signal. Finally the signal is sent to the trigger mechanism which causes the valve to open thereby allowing the passage of fluid from the vessel to the bladder. The valve is capable of being opened by one of the mechanisms described above.

The provision of an oxymeter for measuring the oxygen concentration level in an individual's blood provides an alternative (and potentially additional) mechanism for opening one or more of the valves. This provides a mechanism for opening a valve to provide buoyancy in the event that an abnormal blood oxygen concentration is detected by the oxymeter. In the embodiment of the invention incorporating both an actuator and an oxymeter, this provides a mechanism for the bladder to inflate in situations where the individual wearing the device is submerged in water at insufficient depth for the actuator to be activated but where asphyxiation is suspected (i.e. where an oxymeter measurement indicates that the individual has a low blood oxygen concentration).

In an example of the invention where the device incorporates both an actuator and an oxymeter, an individual wearing the device may be floating on the surface of water face down and hence unable to breathe. In this example the actuator will not be activated if it is not exposed to the predetermined pressure level (i.e. because the individual is floating on the surface of the water). However where an abnormal blood oxygen concentration in the individual is detected (i.e. a low concentration because the individual is not breathing) a valve will be triggered to open by the oxymeter causing the bladder to inflate. In the embodiment of the invention where the bladder is in the form of a jacket and is being worn by the individual around their torso, inflating the bladder will cause the individual's centre of buoyancy and relative position in the water to change such that the individual's head is raised above the level of the water.

In an embodiment of the invention where the device incorporates both an actuator and an oxymeter, there may be situations where a valve is opened as a result of activation by the actuator but the oxymeter mechanism does not cause a valve to be opened. An example of this may be where an individual wearing the device falls into water at a sufficient depth such that the actuator activates as it is exposed to the pre-determined pressure level. In that event the individual wearing the device may be at risk of drowning since they are submerged in water but may not have stopped breathing for long enough to experience blood oxygen concentration levels low enough to trigger the oxymeter mechanism. In this situation the actuator provides the mechanism for opening a valve and subsequently inflating the bladder to provide buoyancy for the individual wearing the device.

In other situations where the device incorporates both an actuator and an oxymeter, it is possible that both the actuator and the oxymeter mechanisms will cause one or more of the valves to be opened concurrently.

While the present invention has been described in detail with reference to certain embodiments, it should be appreciated that the present invention is not limited to those embodiments. In view of the present disclosure, many modifications and variations would present themselves, to those of skill in the art without departing from the scope of various embodiments of the present invention, as described herein. The scope of the present invention is, therefore, indicated by the following claims rather than by the foregoing description. All changes, modifications, and variations coming within the meaning and range of equivalency of the claims are to be considered within their scope.

What is claimed is:

1. A device for providing buoyancy comprising:
   a bladder capable of being inflated;
   a vessel containing fluid for inflating the bladder;
   one or more valves for controlling the passage of fluid between the bladder and the vessel, wherein the one or more valves is capable of being opened to permit the passage of fluid from the vessel to the bladder in response to at least one of exposure of the device to a pre-determined pressure level and detection of a blood oxygen concentration below a pre-determined threshold in an individual using the device;
   an actuator capable of being activated to open at least one of the one or more valves upon being exposed to the pre-determined pressure level; and
   an oxymeter capable of causing at least one of the one or more valves to open upon detecting the blood oxygen concentration below the pre-determined threshold in the blood of the individual,
   wherein the actuator is adjustable to alter the pressure level at which activation occurs and the oxymeter is adjustable to alter the pre-determined oxygen concentration at which it causes the at least one of the one or more valves to open.

2. The device according to claim 1, wherein the actuator comprises a resilient member capable of being compressed by pressure thereby activating the actuator.

3. The device according to claim 1, wherein the actuator comprises a plug magnetically attracted to the interior surface of a conduit or to a component positioned within the conduit and wherein the plug is capable of being dislodged by pressure thereby activating the actuator.

4. The device according to claim 3, wherein the thickness of the plug is capable of being selected to determine the pressure required to dislodge the plug.

5. The device according to claim 3, wherein the weight of the plug is capable of being selected to determine the pressure required to dislodge the plug.

6. The device according to claim 3, wherein the magnetic field strength between the plug and the conduit or between the plug and the component positioned within the conduit is capable of being selected to determine the pressure required to dislodge the plug.

7. The device according to claim 1, wherein the bladder is in the form of any one of a jacket, a belt and a ring for wearing by the individual.

8. The device according to claim 1, wherein the vessel contains compressed fluid capable of being released into the bladder as a gas.

9. The device according to claim 1, wherein the one or more valves is capable of being opened by exposure to liquid released by at least one of the activation of the actuator and the detection of blood oxygen concentration below the pre-determined threshold by the oxymeter.

10. A method for providing buoyancy comprising:
providing a bladder for inflating;
providing a vessel containing fluid for inflating the bladder;
controlling the passage of fluid between the bladder and the vessel with one or more valves;
opening at least one of the one or more valves to permit the passage of fluid from the vessel to the bladder in response to at least one of exposing the device to a pre-determined pressure level and detecting a blood oxygen concentration below a pre-determined threshold in an individual;
providing an actuator capable of being activated to open the at least one of the one or more valves upon being exposed to the pre-determined pressure level;
providing an oxymeter capable of causing the at least one of the one or more valves to open upon detecting the blood oxygen concentration below the pre-determined threshold in the blood of the individual; and
adjusting the actuator to alter the pressure level at which the activation occurs and the oxymeter to alter the pre-determined oxygen concentration at which it causes the at least one of the one or more valves to open.

11. The method according to claim 10, further comprising providing a resilient member to the actuator, the resilient member capable of being compressed by pressure for activating the actuator.

12. The method according to claim 10, further comprising providing a plug to the actuator, wherein the plug is magnetically attracted to the interior surface of a conduit or to a component positioned within the conduit and wherein the plug is capable of being dislodged by pressure for activating the actuator.

13. The method according to claim 12, further comprising selecting the thickness of the plug to determine the pressure required to dislodge the plug.

14. The method according to claim 12, further comprising selecting the weight of the plug to determine the pressure required to dislodge the plug.

15. The method according to claim 12, further comprising selecting the magnetic field strength between the plug and the conduit or between the plug and the component positioned within the conduit to determine the pressure required to dislodge the plug.

16. The method according to claim 10, wherein the step of providing the bladder comprises providing the bladder formed as any one of a jacket, a belt and a ring for wearing by the individual.

17. The method according to claim 10, further comprising containing compressed fluid in the vessel for releasing into the bladder as a gas.

18. The method according to claim 10, further comprising allowing the one or more valves to become opened by exposure to liquid released by at least one of the activation of the actuator and the detection of the blood oxygen concentration below the pre-determined threshold by the oxymeter.

* * * * *